(12) United States Patent
Viitanen et al.

(10) Patent No.: US 8,823,377 B2
(45) Date of Patent: Sep. 2, 2014

(54) METHOD AND APPARATUS FOR VARYING ADAPTIVELY PULSE INTERVAL IN NMR-BASED WATER CONTENT MEASUREMENT

(75) Inventors: Veli-Pekka Viitanen, Huhmari (FI); Sami Virtanen, Espoo (FI)

(73) Assignee: Metso Automation Oy, Vantaa (FI)

( * ) Notice: Subject to any disclaimer, the term of this patent is extended or adjusted under 35 U.S.C. 154(b) by 0 days.

(21) Appl. No.: 13/818,823

(22) PCT Filed: Aug. 30, 2011

(86) PCT No.: PCT/FI2011/050754
§ 371 (c)(1),
(2), (4) Date: Feb. 25, 2013

(87) PCT Pub. No.: WO2012/028786
PCT Pub. Date: Mar. 8, 2012

(65) Prior Publication Data
US 2013/0147482 A1  Jun. 13, 2013

(30) Foreign Application Priority Data
Aug. 31, 2010  (FI) .................................... 20105916

(51) Int. Cl.
*G01V 3/00* (2006.01)
*G01R 33/383* (2006.01)
*G01N 24/08* (2006.01)
*G01R 33/44* (2006.01)

(52) U.S. Cl.
CPC ............ *G01R 33/448* (2013.01); *G01R 33/383* (2013.01); *G01N 24/08* (2013.01)
USPC ........................................ 324/309; 324/307

(58) Field of Classification Search
USPC .................................. 324/309, 307, 306, 300
See application file for complete search history.

(56) References Cited

U.S. PATENT DOCUMENTS

| 4,728,892 A | * | 3/1988 | Vinegar et al. ................. 324/309 |
| 5,015,954 A | * | 5/1991 | Dechene et al. ............... 324/307 |
| 6,392,409 B1 | * | 5/2002 | Chen .............................. 324/303 |
| 6,650,114 B2 | * | 11/2003 | Kruspe et al. .................. 324/303 |
| 2005/0122104 A1 | | 6/2005 | Corver et al. |
| 2011/0316534 A1 | | 12/2011 | Kamar et al. |

FOREIGN PATENT DOCUMENTS

FR  2 786 567 A1  6/2000
WO  WO 03/006974 A1  1/2003

OTHER PUBLICATIONS

"Basic Concepts $T_1$-Relaxation Time," [NMR webcourse material], Queen's University, URL: http://www.chem.queensu.ca/facilities/nmr/nmr/webcourse/t1.htm.

(Continued)

*Primary Examiner* — Louis Arana
(74) *Attorney, Agent, or Firm* — Oliff PLC

(57) ABSTRACT

The invention relates to a NMR method for determining moisture content of a sample, in which method a sample is subjected to a magnetic DC-field, the sample under magnetic DC-field is subjected to a sequence of excitation pulses in RF-frequency with pulse interval for exciting hydrogen nuclei, and NMR signal of the excited hydrogen nuclei is measured. In accordance with the invention spin-lattice relaxation time is estimated for the sample, and pulse interval is adjusted longer than the estimated spin-lattice relaxation time.

19 Claims, 2 Drawing Sheets

(56) References Cited

OTHER PUBLICATIONS

"The Basics of NMR; Chapter 11; Advanced Spectroscopic Techniques," URL: http://replay.waybackmachine.org/20090227121252/http://www.cis.rit.edu/htbooks/nmr/chap-11/chap-11.htm.

Sep. 27, 2012 International Preliminary Report on Patentability issued in International Application No. PCT/FI2011/050754.
Feb. 16, 2012 International Search Report issued in International Application No. PCT/FI2011/050754.

* cited by examiner

METHOD AND APPARATUS FOR VARYING ADAPTIVELY PULSE INTERVAL IN NMR-BASED WATER CONTENT MEASUREMENT

The invention relates to a method for varying adaptively pulse interval in NMR-based water content measurement according to the preamble of claim 1.

The invention also relates to an apparatus for adaptive pulse interval adjustment in NMR-based water content measurement.

NMR-technology (Nuclear Magnetic Resonance) has been used for determining moisture content of materials. For example FR 2786567 describes this kind of a system. The present systems are clumsy and expensive and therefore used rarely in commercial application.

It is an object of the present invention to provide a novel type of NMR-based water content measurement capable of overcoming at least some problems of the prior-art technology described in the foregoing.

The invention is based on the concept of using such pulse sequences, where the rate of pulses is optimized for different humidity levels of the sample to be measured. The said optimization is advantageously based on estimating the so-called spin-lattice relaxation time constant.

Furthermore, also the measuring equipment is characterized by using low energy magnetic field and a weighing apparatus.

More specifically, the method according to the invention is characterized by estimating spin-lattice relaxation time for each sample on the basis of response to the sequence of excitation pulses, and adjusting the pulse interval at its minimum while keeping the pulse interval longer than the estimated spin-lattice relaxation time.

Furthermore, the apparatus according to the invention is characterized by estimating spin-lattice relaxation time for each sample on the basis of response to the sequence of excitation pulses generated by a sequence of excitation pulses in RF-frequency for the sample under a magnetic DC-field, and adjusting the pulse interval at its minimum while keeping the pulse interval longer than the estimated spin-lattice relaxation time.

The invention offers significant benefits.

Firstly, the measurement time may be minimized for all humidities and sample materials.

Secondly, the measurement equipment is light weight and inexpensive without compromising the measurement accuracy.

Figure 1:
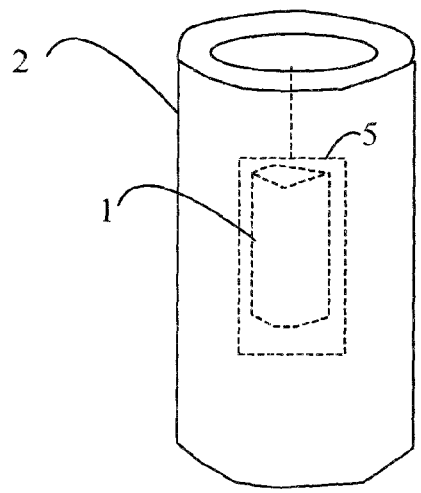

In the following, the invention will be examined with the help of exemplifying embodiments illustrated in the appended drawings in which FIG. 1 presents schematically the basic conception of the NMR-humidity measurement equipment suitable for the invention.

Figure 2:
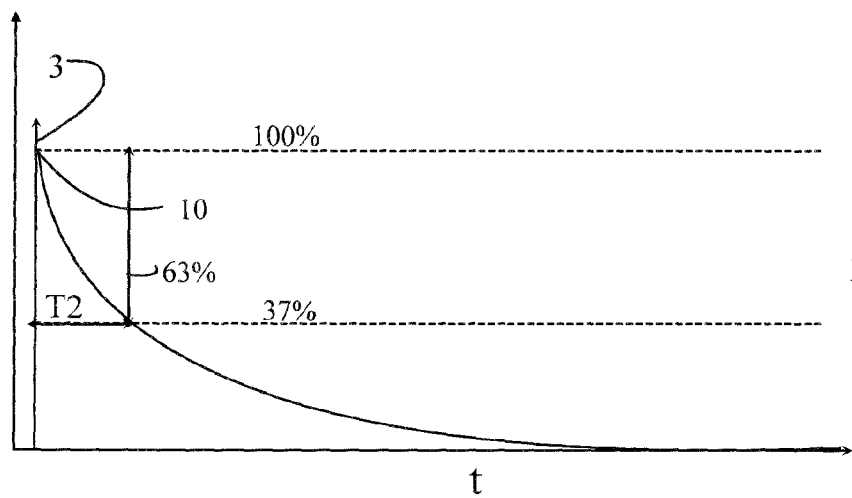

FIG. 2 presents graphically typical NMR signals with their relaxation times.

Figure 3:
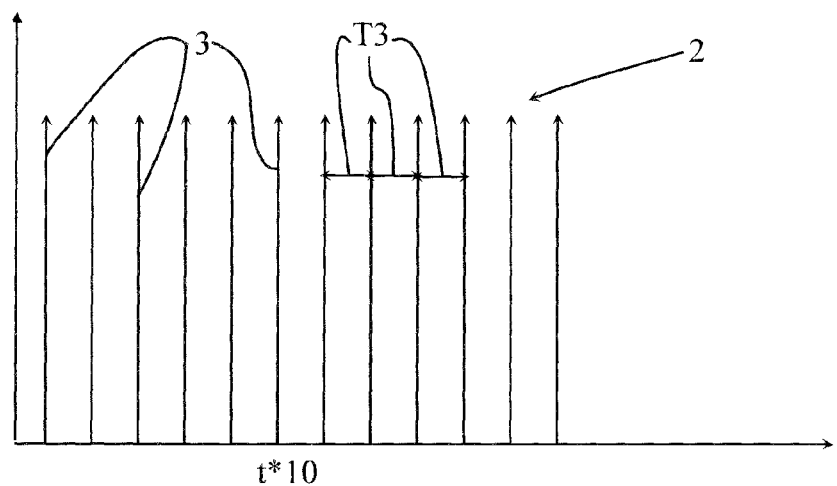

FIG. 3 presents a typical pulse sequence in accordance with the invention.

Figure 4:
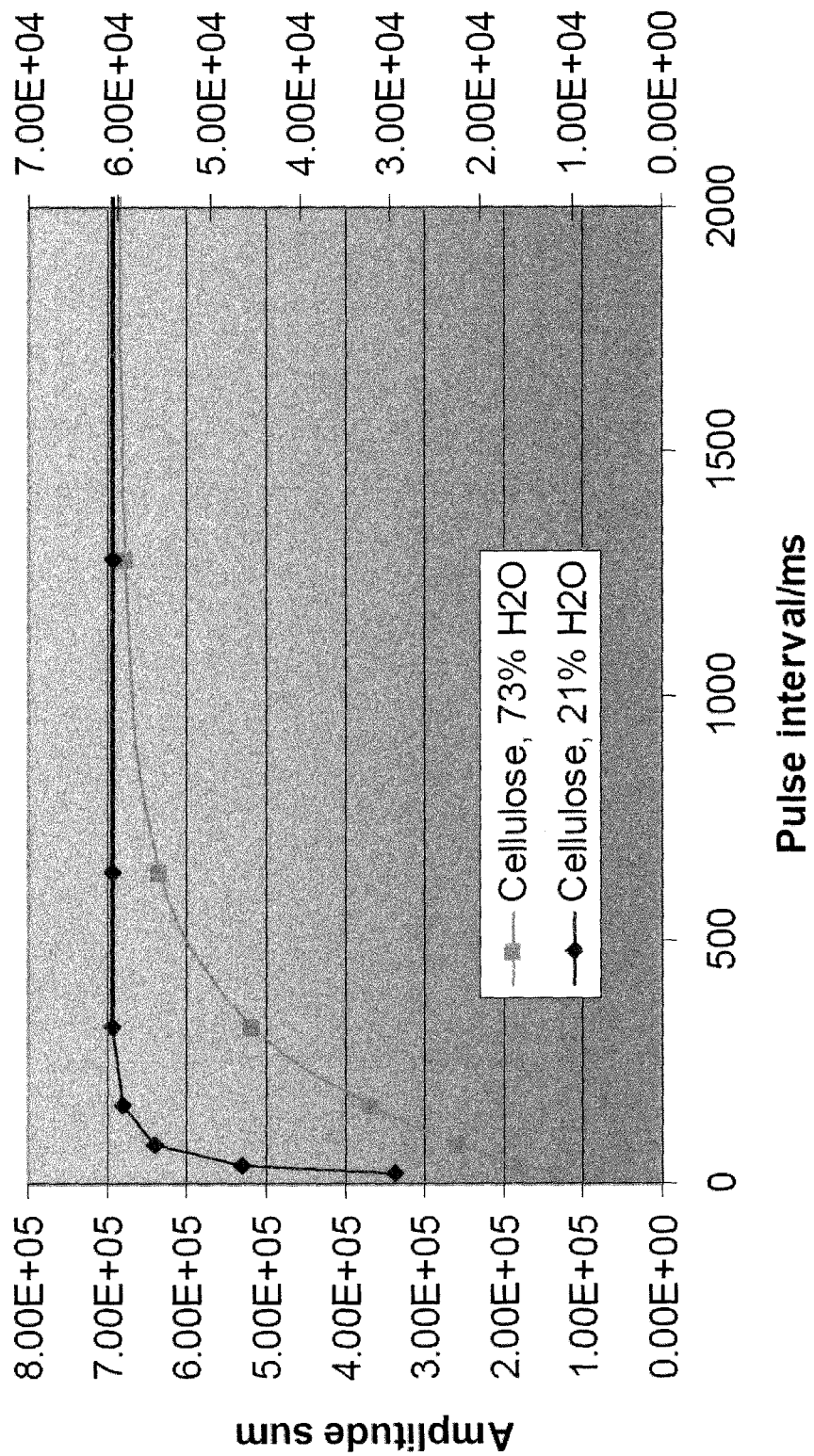

FIG. 4 shows graphically an example of the effect of the pulse interval on the amplitude sum over a large number of pulses.

In accordance with FIG. 1 in NMR—humidity measurement a homogeneous DC-Magnetic field is generated by a magnet 2 into the a sample 1 to be measured, then interaction of the magnetic field with the hydrogen in the sample 1 causes a small magnetization to develop in the sample 1. Next, the sample 1 is exposed to a short intense radio frequency (RF) excitation pulse 3 (FIGS. 2 and 3) by a transmitter/receiver 5, which excites the hydrogen nuclei. In the following step the measurement instrument 5 records the NMR signal (known as a Free Induction Decay or FID) for a period of milliseconds. During this time, some parts of the sample undergo NMR relaxation and return to the original state. The signal amplitude 10 (FIG. 2) at predetermined time (tens of microseconds following the first RF pulse) is proportional to the total amount of hydrogen from moisture of the samples. Therefore, the maximum value of NMR-signal defines the moisture content. In practice this maximum value 10 is often extrapolated from a measurement performed some time after the real maximum 10.

Nuclear Magnetic Resonance-based instrument can easily be configured to yield an electrical signal that is proportional to the content of hydrogen containing liquids in a solid material. The NMR-device is especially well suited for measuring the water content in biomass. When the sample to be measured is very dry, typically meaning water content of less than 20 m-%, the signal-to-noise-ratio is low, which is typically compensated for by increasing the number of successive measurements and averaging them. This easily leads to a long measurement time. The limitation for the time between successive measurements is primarily set by the so-called spin-lattice relaxation time (hereafter called T1). This is the time required for the deflected average magnetization vector to recover its original value. The recovery is enabled by energy dissipation from the protons to the lattice. If the excitation pulse is applied before the full relaxation, reduced signal amplitude is observed, and the correlation coefficient between the water content and the signal amplitude is altered, and thus calibration will not be valid.

T1 is essentially a function of interaction between the nuclear spin and the lattice. Generally, the drier the material the shorter the corresponding T1. This phenomenon can be utilized in optimizing the pulse interval, meaning that S/N-ratio for dry samples can be increased significantly for a given total measurement time.

T1 is the time it takes for the nuclear magnetisation to recover approximately 63% [1−(1/e)] of its initial value after being flipped into the magnetic transverse plane. Different tissues have different T1 values. For example, fluids have long T1 (1500-2000 ms), and water based tissues are in the 400-1200 ms range.

In accordance with FIG. 2, T2 characterizes the rate at which the $M_{xy}$ component of the magnetization vector decays in the transverse magnetic plane. It is the time it takes for the transverse magnetisation to reach 37% (1/e) of its initial magnitude after flipping into the magnetic transverse plane. Hence the relation:

$$M_{xy}(t)=M_{xy}(0)e^{-t/T2}$$

T2 decay occurs typically 5 to 10 times more rapidly than T1 recovery, and different tissues have different T2s. For example, fluids have the longest T2s (700-1200 ms), and water based tissues are in the 40-200 ms range.

The method consists typically of two steps:
1. Estimating the T1 Time for the Sample.

This can be achieved in accordance with FIGS. 2 and 3 e.g. by measuring the response signal amplitude 10 using successive excitation pulse sequences 2 with a constant number of pulses 3 and a stepwise increasing pulse interval T3, and detecting the minimum interval T3 required for the response signal to remain at the constant (maximum) level 10. As told earlier, the maximum value 10 may be determined by extrapolation from a delayed measurement. Estimation of T1 can be performed in a few seconds.

Another method of estimating T1 is to measure the spin-spin relaxation time T2, and estimate T1 from T2. Typically both decrease when the water content of the sample decreases. Actually the T2 is usually estimated based on the measured value of T2*, which is a combined result of spin-spin-relaxations and decoherence effect caused by inhomogeneity of the primary magnetic field being device specific. A third method of estimating T1 comprises the use of two successive excitation pulse sequences, each of which is preceded by a so-called saturation pulse sequence. The pulse interval in the said excitation pulse sequences is advantageously larger than T2*, but preferably not significantly smaller than T1. The two successive excitation pulse sequences shall have different pulse intervals t1 and t2, e.g. t1=T1 and t2=(2*T1). The ratio of signal amplitudes A1/A2 obtained with pulse interval t1 and t2, respectively, can be calculated from the following equation:

$$\frac{A1}{A2} = \frac{\left(1 - \exp\left(\frac{-t1}{T1}\right)\right)}{\left(1 - \exp\left(\frac{-t2}{T1}\right)\right)}$$

Which can be solved numerically for T1.

Yet another means to estimate T1 is to use the water signal amplitude per unit mass of sample: the lower the said ratio is (the dryer the sample is), the shorter is the T1. This estimation method is valid only for a limited range of samples, for example solid biofuels.

Yet another method of estimating T1 comprises the use of two successive excitation pulse sequences, each of which is optionally preceded by a so-called saturation pulse sequence.

Without the saturation pulse sequences, the estimate for T1 can be numerically solved from the equation:

$$\frac{\sum A1}{\sum A2} = \frac{1 + (n-1)*\left(1 - \exp\left(\frac{-t1}{T1}\right)\right)}{1 + (n-1)*\left(1 - \exp\left(\frac{-t2}{T1}\right)\right)}$$

The methods described above are only examples of the possible means to estimate T1.

2. Performing the Actual Measurement Using the Minimum Pulse Interval that Yields a Constant (Maximum) Amplitude with Sufficient, e.g. 1% Accuracy.

Typically, such minimum pulse interval T3 is 5*T1. In this way, the number of averaged pulses within 20 s measurement time frame can be increased from approx. 10 (long pulse interval required by wet samples) to approx. 200 (short pulse interval enabled by very dry samples), thus improving the S/N by a factor of sqrt(200/10)=4.5.

Low NMR signal-to-noise ratio typically obtained from dry samples can be enhanced by shorter measurement interval and thus larger number of individual measurements. The optimum pulse interval is determined using a probe pulse sequence to estimate the spin-lattice relaxation time constant T1, which advantageously can be used as an input for calculating the low limit for the pulse interval. The disclosed method can improve S/N ratio of very dry samples by a factor of five.

As can be seen from FIG. 4 the sample with medium moisture content can be measured with shorter pulse interval than the wet sample.

What is claimed is:

1. A Nuclear Magnetic Resonance (NMR) method for determining moisture content of a sample, the method comprising the steps of:
    subjecting a sample to a magnetic DC-field,
    subjecting the sample under the magnetic DC-field to a sequence of excitation pulses in RF-frequency with pulse interval for exciting hydrogen nuclei, and
    measuring an NMR signal of the excited hydrogen nuclei,
        wherein the measuring the NMR signal further comprises the steps of:
        estimating a spin-lattice relaxation time for each sample on the basis of a response to the sequence of excitation pulses, and
        adjusting the pulse interval at its minimum while keeping the pulse interval longer than the estimated spin-lattice relaxation time.

2. The method in accordance with claim 1, wherein in the measuring the NMR signal, the pulse interval is adjusted to be more than five times the spin-lattice relaxation time.

3. The method in accordance with claim 1, wherein in the estimating the spin-lattice relaxation time, measuring an amplitude of the NMR signal using successive excitation pulse sequences with a constant number of pulses and a stepwise increasing pulse interval, and detecting the minimum interval required for the signal to remain essentially at its maximum value.

4. The method in accordance with claim 1, in the measuring the NMR signal, determining the spin-spin relaxation time either directly or indirectly and spin-lattice relaxation time is estimated from the spin-spin relaxation time.

5. The method in accordance with claim 4, wherein the estimating the spin-spin relaxation time is based on a measured value of T2*, T2* being a combined result of spin-spin-relaxations and decoherence effect caused by inhomogeneity of a primary magnetic field of the magnetic DC-field.

6. The method in accordance with claim 1, wherein in the measuring the NMR signal, using two successive excitation pulse sequences, each of the two successive excitation pulse sequences being preceded by a saturation pulse sequence, the saturation pulse sequence having a pulse interval longer than the measured spin-spin relaxation time, but not significantly shorter than the spin-lattice relaxation time such that the two successive excitation pulse sequences have a first pulse interval t1 and a second pulse interval t1, the first pulse interval t1 being shorter than the second pulse interval t2, and
    forming a spin-lattice relaxation time on the basis of a ratio of a first signal amplitude A1 to a second signal amplitude A2, wherein the first signal amplitude A1 is based on the first pulse interval pulse interval t1 and the second signal amplitude A2 is based on the second pulse interval t2.

7. The method in accordance with claim 1, the method further comprising actually measuring the NMR signal using a minimum pulse interval of the RF excitation pulse that yields a constant maximum amplitude with 1% accuracy.

8. The method in accordance with claim 7, wherein in the actually measuring the NMR signal, a third pulse interval t3 is used as a minimum pulse interval T3 having a value of five times the estimated spin-lattice relaxation time.

9. The method in accordance with claim 1, wherein in the measuring the NMR signal, an optimum pulse interval is determined using a probe pulse sequence to estimate a spin-lattice relaxation time constant, which is used as an input for calculating a low limit for the pulse interval.

10. The method in accordance with claim 6, wherein in the forming the spin-lattice relaxation time, the saturation pulse sequence is omitted and the estimate for the spin-lattice relaxation time T1 is numerically solved from the equation:

$$\frac{\sum A1}{\sum A2} = \frac{1+(n-1)*\left(1-\exp\left(\frac{-t1}{T1}\right)\right)}{1+(n-1)*\left(1-\exp\left(\frac{-t2}{T1}\right)\right)},$$

wherein n is a number of pulses, and $\Sigma A1$, $\Sigma A2$ are the sums of the first signal amplitudes A1 and the second signal amplitudes A2 obtained with first pulse intervals pulse intervals t1 and second pulse intervals t2, respectively.

11. A moisture content determining Nuclear Magnetic Resonance (NMR) device, the device comprising:
a space reserved for a sample;
a DC-magnet surrounding the space reserved for the sample;
a transmitter that generates a sequence of excitation pulses in RF-frequency subjecting the samples to a magnetic DC-field; and
a measurement instrument that measures a NMR signal of the excited hydrogen nuclei,
wherein the measurement instrument estimates spin-lattice relaxation time for each sample on the basis of a response to the sequence of excitation pulses generated by said transmitter, and adjusting a pulse interval at its minimum while keeping the pulse interval longer than the estimated spin-lattice relaxation time.

12. The device in accordance with claim 11, the measurement instrument estimates spin-lattice relaxation time by measuring an amplitude of the NMR signal using successive excitation pulse sequences with a constant number of pulses and a stepwise increasing pulse interval, and detects the minimum interval required for the signal to remain essentially at its maximum value.

13. The device in accordance with claim 11, wherein the measurement device determines the spin-spin relaxation time either directly or indirectly and estimates the spin-lattice relaxation time from the spin-spin relaxation time.

14. The device in accordance with claim 13, wherein the measurement device estimates the spin-spin relaxation time based on a measured value of T2*, T2* being a combined result of spin-spin relaxations and decoherence effect caused by inhomogeneity of a primary magnetic field of the DC-field.

15. The device in accordance with claim 11, wherein the transmitter generates two successive excitation pulse sequences, each of the two successive excitation pulse sequences being preceded by a saturation pulse sequence, the saturation pulse sequence being larger than the measured spin-spin relaxation time, but not significantly smaller than the spin-lattice relaxation time such that the two successive excitation pulse sequences have a first pulse interval t1 and a second pulse interval t1, the first pulse interval t1 being shorter than the second pulse interval t2, and the measurement device estimates a spin-lattice relaxation time on the basis of a ratio of a first signal amplitude A1 to a second signal amplitude A2, wherein the first signal amplitude A1 is based on the first pulse interval pulse interval t1 and the second signal amplitude A2 is based on the second pulse interval t2.

16. The device in accordance with claim 11, the measurement device actually measures the NMR signal using a minimum pulse interval of the RF excitation pulse that yields a maximum constant amplitude with 1% accuracy.

17. The device in accordance with claim 16, wherein the measurement device uses a third pulse interval t3 as a minimum pulse interval T3 having a value of five times the estimated spin-lattice relaxation time.

18. The device in accordance with claim 11, the measurement device determining the optimum pulse interval using a probe pulse sequence to estimate a spin-lattice relaxation time constant, which sets a low limit for the pulse interval.

19. The device in accordance with claim 15, wherein the means for saturation pulse sequence is omitted, and the measurement device numerically estimates the spin-lattice relaxation time T1 from the equation:

$$\frac{\sum A1}{\sum A2} = \frac{1+(n-1)*\left(1-\exp\left(\frac{-t1}{T1}\right)\right)}{1+(n-1)*\left(1-\exp\left(\frac{-t2}{T1}\right)\right)},$$

wherein n is a number of pulses, and $\Sigma A1$, $\Sigma A2$ are the sums of the first signal amplitudes A1 and the second signal amplitudes A2 obtained with first pulse intervals t1 and second pulse intervals t2, respectively.

* * * * *